United States Patent [19]

Barreau et al.

[11] Patent Number: 5,403,852
[45] Date of Patent: Apr. 4, 1995

[54] OXAZOLE DERIVATIVES, THEIR PREPARATION AND PHARMACEUTICAL COMPOSITIONS CONTAINING THEM

[75] Inventors: Michel Barreau, Montgeron; Michel Kryvenko, Paris; Marc-Pierre Lavergne, Mandres les Roses; Auguste Techer, Avon, all of France

[73] Assignee: Laboratoire Roger Bellon, Nerilly-Seie, France

[21] Appl. No.: 960,428

[22] PCT Filed: Jun. 13, 1991

[86] PCT No.: PCT/FR91/00473

§ 371 Date: Dec. 11, 1992

§ 102(e) Date: Dec. 11, 1992

[87] PCT Pub. No.: WO91/19714

PCT Pub. Date: Dec. 26, 1991

[30] Foreign Application Priority Data

Jun. 14, 1990 [FR] France .................. 90 07388

[51] Int. Cl.⁶ ............................................ A61K 31/42
[52] U.S. Cl. .................................... 514/374; 548/235; 548/236
[58] Field of Search ................ 514/374; 548/235, 236

[56] References Cited

U.S. PATENT DOCUMENTS

| | | | |
|---|---|---|---|
| 3,546,342 | 12/1970 | Brown | 548/236 |
| 3,574,228 | 4/1971 | Brown | 548/236 |
| 3,586,679 | 6/1971 | Tandon et al. | |
| 3,933,840 | 1/1976 | Dahm et al. | 548/229 |
| 4,051,250 | 9/1977 | Dahm et al. | 548/229 |
| 5,262,540 | 11/1993 | Meanwell | 514/374 |

FOREIGN PATENT DOCUMENTS 1381860  1/1975  United Kingdom .

*Primary Examiner*—Donald G. Daus
*Attorney, Agent, or Firm*—James A. Nicholson; Martin F. Savitzky; Raymond S. Parker, III

[57] ABSTRACT

Oxazole derivatives of the formula

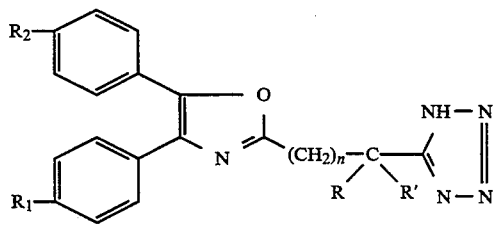

wherein R and R' are each hydrogen or alkyl containing 1 or 2 carbon atoms, $R_1$ and $R_2$ are the same or different and represent hydrogen, halogen or straight- or branched-chain ($C_{1-4}$) alkyloxy radicals, and n is 3-6; their salts their isomers and mixtures and their preparation method, are method are described. These derivatives display anti-inflammatory activity.

8 Claims, No Drawings

OXAZOLE DERIVATIVES, THEIR PREPARATION AND PHARMACEUTICAL COMPOSITIONS CONTAINING THEM

The present invention relates to new oxazole derivatives of general formula:

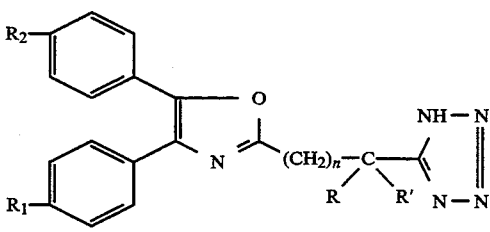

(I)

in which:
R and R' are identical or different and represent a hydrogen atom or an alkyl radical containing 1 or 2 carbon atoms,
$R_1$ and $R_2$ are identical or different and represent hydrogen or halogen atoms or alkyloxy radicals in which the alkyl portion contains 1 to 4 carbon atoms in a straight or branched chain, and
n equals 3 to 6,
as well to their salts, to their isomers where they exist and to pharmaceutical compositions containing them.

In British Patent GB 1,381,860, tetrazole derivatives of structure:

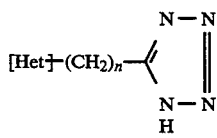

have been described, in which structure [Het] is a 5-member heterocycle of general formula:

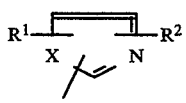

it being possible for to be O or S and $R^1$ and $R^2$ being substituted or unsubstituted aryl groups, and n equals 0, 1 or 2.

These derivatives manifest anti-inflammatory activity.

In Patent Application FR 1,584,222, oxazole derivatives of general formula:

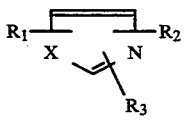

have been described, in which formula $R_1$ and $R_2$ are identical or different and represent phenyl radicals optionally substituted with halogen, alkyl, alkyloxy, nitro or amino, X is an oxygen or sulphur atom and $R_3$ is an aliphatic acid radical containing 2 to 6 carbon atoms.

These products display anti-inflammatory activity.

In Patent Application DE 2,129,012, -azole derivatives of general formula:

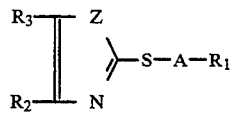

have been described, in which formula $R_1$ is a carboxyl group, $R_2$ and $R_3$ are optionally substituted aryl groups, A is $C_nH_{2n}$ and Z is a sulphur or oxygen atom.

These products are useful as anti-inflammatories.

It has now been found that the oxazole derivatives according to the invention, which possess long chains separating the heterocycles, manifest an antagonist action on the effects of leukotriene $B_4$ which was not possessed or was barely possessed by the products of the prior art.

Leukotriene $B_4$ is a potent mediator of inflammation which is formed following the bioconversion of arachidonic acid by means of 5-lipoxygenase. It contributes, in particular, to phenomena such as chemotaxis, cell activation and exocytosis of enzymes, and also participates in immunological and tissue disturbances. The products according to the invention are hence especially advantageous in the treatment of diseases in which this mediator plays a part, in particular in the treatment of inflammatory diseases, for which the products of the prior art were ineffective.

In the general formula (I), when the radicals $R_1$ and/or $R_2$ represent halogen atoms, they may be chosen from fluorine, chlorine or bromine atoms. Preferably, they represent a chlorine atom. The symbol n is between 3 and 6, but the chosen value of n will preferably be 4 or 5.

According to the invention, the new oxazole derivatives may be prepared by the action of an alkali metal azide or tri-n-butyltin azide on a nitrile of general formula:

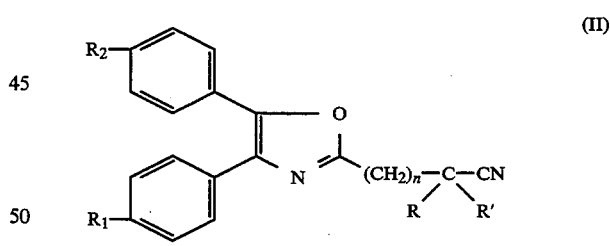

(II)

in which R, R', $R_1$, $R_2$ and n are defined as above.

When an alkali metal azide is reacted, the action of sodium azide is advantageously employed. The reaction is performed in the presence of ammonium chloride or the hydrochloride of a nitrogenous organic base (for example triethylamine, di-n-butylamine), in an organic solvent such as an amide (for example dimethylformamide, N,N-dimethylacetamide, N-methylpyrrolidone), at a temperature of between 80° and 150° C., and preferably between 80° and 110° C. When the action of tri-n-butyltin azide is employed, the reaction is performed in 1,2-dimethoxyethane at the temperature defined hereinbefore.

The nitrile of general formula (II) for which R or R' is a hydrogen atom may be prepared by hydrolysis of the cyano ester of general formula:

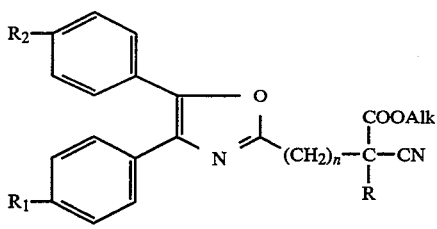 (III)

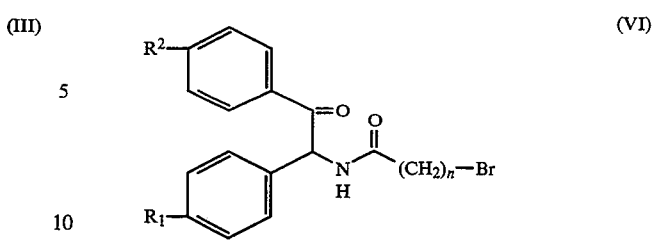 (VI)

in which R, $R_1$, $R_2$ and n are defined as above and Alk represents a linear or branched alkyl radical containing 1 to 4 carbon atoms, followed by decarboxylation of the acid obtained.

The hydrolysis of the ester may be carried out in an acidic or basic medium. When the hydrolysis is carried out in acidic medium, the reaction is performed, for example, by the action of p-toluenesulphonic acid or formic acid at a temperature of between 100° and 130° C. When the hydrolysis is carried out in a basic medium, the action of an alkali metal base such as sodium hydroxide or potassium hydroxide, in aqueous-alcoholic solution (for example in a methanol-water, ethanol-water or methoxyethanol-water medium), at a temperature of between 5° and 50° C., is advantageously employed.

The decarboxylation of the acid is performed by heating to a temperature Of between 100° and 200° C.

The cyano ester of general formula (III) may be prepared by the action of a cyanoacetate of general formula:

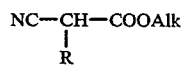 (IV)

in which Alk and R are defined as hereinbefore, on the bromo derivative of general formula:

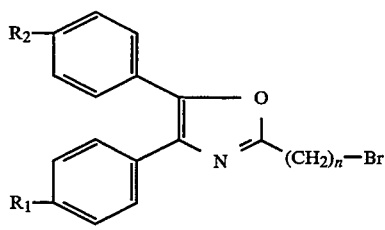 (V)

in which $R_1$, $R_2$ and n are defined as above.

The reaction is catalysed by tetrabutylammonium iodide; it is performed in the presence of an acid-acceptor, for example an alkali metal carbonate (potassium carbonate), in a polar aprotic solvent. The reaction is advantageously performed in dimethylformamide at a temperature of between 50° and 110° C.

It is not essential to purify the product obtained in order to employ it in the following reaction.

The bromo derivative of general formula (V) may be obtained by cyclisation of the keto amide of general formula:

in which $R_1$, $R_2$ and n are defined as above.

The reaction is performed in the presence of a dehydrating agent such as, for example, phosphorus oxychloride, thionyl chloride or chlorosulphonic acid, or in the presence of an arylsulphonyl chloride (benzenesulphonyl chloride, tosyl chloride) in pyridine. The reaction is performed with or without a solvent at a temperature of between 5° and 150° C. When the reaction is performed in a solvent, the latter is advantageously chosen from cyclohexane, aromatic solvents (toluene) or chlorinated solvents (methylene chloride, 1,2-dichloroethane).

The bromo derivative of general formula (VI) may be obtained by the action of an acid chloride of general formula:

 (VII)

$$Cl—CO—(CH_2)_n—Br$$

in which n is defined as above, on the hydrochloride of the amino ketone of general formula:

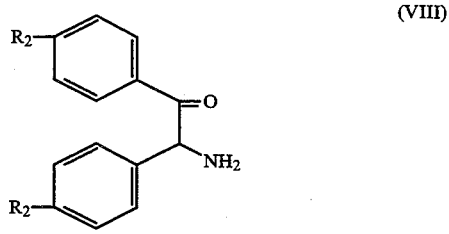 (VIII)

in which $R_1$ and $R_2$ are defined as above.

The reaction is generally performed in the presence of an excess of the acid chloride of general formula (VII) and a nitrogenous base such as pyridine or a tertiary amine (for example triethylamine, N-methylmorpholine or N,N-dimethylaniline) or an alkali metal carbonate. The reaction is advantageously performed in a chlorinated solvent (chloroform, methylene chloro), in an ether (ethyl ether, tetrahydrofuran, dioxane, 1,2-dimethoxyethane) or in an aliphatic or aromatic hydrocarbon, at a temperature of between 5° and 120° C.

The hydrochloride of the amino ketone of general formula (VIII) may be prepared according to the methods described by:

G. Drefahl et al., Ann. Chem., 589, 82 (1954) and J. Prakt. Chem., 3, 307 (1966);

M. J. Hatch et al., J. Am. Chem. Soc., 75, 38 (1953);

H. O. House et al., J. Org. Chem., 28, 307 (1963); or as described below in the examples.

The nitrile of general formula (II) in which R and R' represent hydrogen atoms may also be obtained by the action of an alkali metal cyanide on a bromo derivative of general formula:

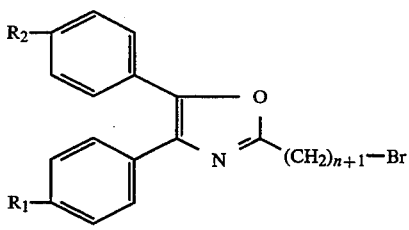

in which R₁, R₂ and n are defined as above.

The reaction is generally performed in an aqueous-alcoholic medium at the refluxing temperature of the reaction mixture. The action of potassium cyanide in an aqueous-ethanolic medium is advantageously employed.

The bromo derivative of general formula (IX) may be prepared by a procedure similar to that used for the preparation of the bromo derivative of general formula (V).

The nitrile of general formula (II) in which R and R' simultaneously represent alkyl radicals may be prepared by the action of a nitrile of general formula:

in which R and R' are defined as in hereinbefore, on a bromo derivative of general formula (V).

The reaction is advantageously performed in the presence of lithium diisopropylamide in an organic solvent or a mixture of solvents such as, for example, tetrahydrofuran and toluene, at a temperature in the region of −70° C.

The nitrile of general formula (II) for which R is hydrogen and R' is alkyl may be also be prepared by cyclisation of the nitrile of general formula:

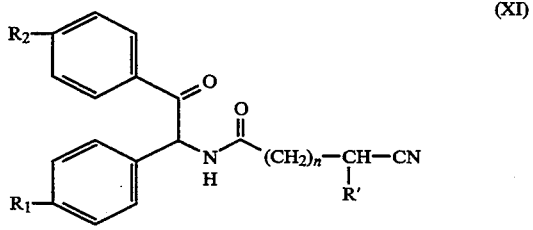

in which R₁, R₂ and n are defined as above and R' is defined as hereinbefore.

The reaction is performed under the conditions described above for the cyclisation of a derivative of general formula (VI).

The nitrile of general formula (XI) may be obtained by the action of an acid chloride of general formula:

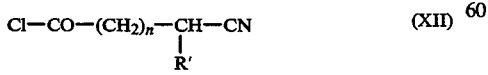

in which n and R' are defined as above for the general formula (XI), on the hydrochloride of the amino ketone of general formula (VIII).

The reaction is performed under conditions similar to the conditions described for the reaction of the acid chloride of general formula (VII) with the hydrochloride of the amino ketone of general formula (VIII).

The acid chloride of general formula (XII) may be prepared as described below in the examples, or by a procedure similar to that used in this method.

The products according to the invention may be purified by crystallisation or by chromatography.

Where appropriate, the isomers of the products according to the invention may be separated according to the usual methods which do not adversely effect the remainder of the molecule. For example, they may be separated by chromatography on a chiral column.

The products according to the present invention may be converted to metal salts according to methods known per se. These salts may be obtained by the action of a strong metallic base on a product according to the invention in a suitable solvent. The salt formed precipitates, where appropriate after concentration of its solution; it is separated by filtration, decantation or lyophilisation.

As examples of pharmaceutically acceptable salts, the salts with alkali metals (sodium, potassium, lithium) may be mentioned.

The new oxazole derivatives of general formula (I) and their salts are especially advantageous in the field of inflammation in which leukotriene B₄ is involved, in particular in the osteoarticular field. As a result of their affinity for leukotriene B₄ receptors, they interfere with this agonist by blocking its action as receptor level.

It has been possible to demonstrate their affinity for leukotriene B₄ receptors by measuring their effect with respect to the binding to tritiated leukotriene B₄ on guinea pig spleen membranes, according to a method based on the method of J. B. Cheng, J. of Pharmacology and Experimental Therapeutics, 236, 126 (1986). In this technique, the products according to the invention were shown to be active at concentrations of between 5 and 500 nM (IC₅₀).

The products selected also showed that they were leukotriene B₄ antagonists, by counteracting in vivo the cellular afflux induced by injection of LTB₄ into the mouse peritoneum, according to a technique based on the method described by D. E. Griswold et al., Inflammation, 13 (6), 727 (1989). In this technique, the products were shown to be active orally at doses of between 20 and 100 mg/kg.

In addition, the products according to the invention have the advantage of being of very low toxicity. Administered orally, their toxicity (LD₅₀) in mice is between 200 mg/kg and values above 1 g/kg.

Particularly advantageous are the oxazole derivatives for which:

R and R', which may be identical or different, are hydrogen atoms or methyl radicals, R₁ and R₂, which may be identical or different, represent hydrogen or chlorine atoms or methoxy radicals, and n equals 4 or 5, and among these products more especially the following oxazole derivatives:

5-{6-[4,5-bis(4-methoxyphenyl)-2-oxazolyl]hexyl}tetrazole;

5-{7-[4,5-bis(4-methoxyphenyl)-2-oxazolyl]-2-heptyl}-1H-tetrazole;

5-{7-[4,5-bis(4-methoxyphenyl)-2-oxazolyl]-2-methyl-2-heptyl}-1H-tetrazole;

5-{5-[4,5-bis(4-methoxyphenyl)-2-oxazolyl]pentyl} tetrazole;

5-{6-[4-(4-chlorophenyl)-5-(4-methoxyphenyl)-2-oxazolyl]hexyl}tetrazole.

The examples which follow, given without implied limitation, illustrate the present invention.

EXAMPLE 1

42 g of 7-[4,5-bis(4-methoxyphenyl)-2-oxazolyl]heptanenitrile, dissolved in 850 cm$^3$ of dimethylformamide, are heated with stirring to 105° C. for 50 hours with 21 g of sodium azide and 17.3 g of ammonium chloride.

The mixture is then brought back to room temperature, treated with a further quantity of sodium azide (21 g) and ammonium chloride (17.3 g) and thereafter stirred again at 105° C. for 60 hours. After cooling, the insoluble products are separated by filtration, and the solution is diluted with 2550 cm$^3$ of water, then taken to pH 3 with 2N hydrochloric acid and extracted with 3 times 300 cm$^3$ of ethyl acetate. The combined organic solutions are washed by shaking and allowing settling to take place, first with 3 times 300 cm$^3$ of water and then with twice 100 cm$^3$ of saturated aqueous sodium chloride solution. After drying over magnesium sulphate, the solvent is evaporated off under reduced pressure (5.2 kPa). The evaporation residue is chromatographed on a column of internal diameter 5.8 cm containing 420 g of silica (50 to 200μ). The column is eluted, collecting 200 cm$^3$ fractions, with 4.2 liters of diisopropyl ether, then with 2 liters of a diisopropyl ether/ethyl acetate (70:30 by volume) mixture and finally with 2.2 liters of diisopropyl ether/ethyl acetate (50:50). The solid residues resulting from evaporation of the fractions from the last eluent mixture are combined and recrystallised in 130 cm$^3$ of ethyl acetate. 20.4 g (43.7%) of 5-{6-[4,5-bis(4-methoxyphenyl)-2-oxazolyl]hexyl}tetrazole are obtained in the form of white crystals, melting point 124° C.

7-[4,5-Bis(4-methoxyphenyl)-2-oxazolyl]heptanenitrile may be prepared as follows:

67.5 g of 7-[4,5-bis(4-methoxyphenyl)-2-oxazolyl]-2-cyanoheptanoic acid are heated to 180° C. until the evolution of carbon dioxide has ceased (7 hours). After cooling, the residual oil is dissolved in 400 cm$^3$ of ethyl ether. The ethereal solution is washed with 3 times 50 cm$^3$ of saturated aqueous sodium bicarbonate solution and 100 cm$^3$ of water, dried over magnesium sulphate and filtered, and the solvent is removed. The evaporation residue is chromatographed on a column 5.8 cm$^3$ in diameter containing 360 g of silica gel (50 to 200μ). The column is eluted, collecting 250 cm$^3$ fractions, with 3.5 liters of a diisopropyl ether/ethyl acetate (70:30 by volume) mixture. The fractions emerging at between 0.5 and 3.5 liters are concentrated to dryness. 52.3 g (75.9%) of 7-[4,5-bis(4-methoxyphenyl)-2-oxazolyl]heptanenitrile are thereby obtained in the form of an oil, which is used directly in the above reaction.

7-[4,5-Bis(4-methoxyphenyl)-2-oxazolyl]-2-cyanoheptanoic acid may be prepared in the following manner: 53 cm$^3$ of phosphorus oxychloride are added with stirring to a solution of 84.8 g 1,2-bis(4-methoxyphenyl)-2-(6-bromohexanamido)ethanone in 320 cm$^3$ of toluene. The mixture is heated to 80° C. for 4 hours and then concentrated to dryness under reduced pressure (5.2 kPa). 250 cm$^3$ of ice-cold water are added to the residue and the mixture is extracted with dichloromethane (3 times 150 cm$^3$). The combined organic extracts are washed with water (twice 100 cm$^3$) and saturated aqueous sodium bicarbonate solution (twice 100 cm$^3$) and dried over magnesium sulphate. After filtration, the organic phase is concentrated to dryness under reduced pressure (0.2 kPa) and 78.1 g (95.9%) of a viscous oil are obtained.

The latter is dissolved in 75 cm$^3$ of dimethylformamide and the solution is added to a mixture of 103 g of ethyl cyanoacetate, 6.7 g of tetrabutylammonium iodide and 25 g of potassium carbonate in 550 cm$^3$ of dimethylformamide. The suspension is stirred at 60° C. for 12 hours. After cooling, 2.5 liters of water are added and the mixture is extracted with diethyl ether (3 times 500 cm$^3$). The combined ethereal extracts are washed with 3 times 75 cm$^3$ of water, dried over magnesium sulphate, filtered and concentrated to dryness under reduced pressure (5.2 kPa). The residue is chromatographed on a column 5.8 cm in diameter containing 300 g of silica gel. The column is eluted, collecting 200 cm$^3$ fractions, with 2 liters of a mixture containing equal parts of diisopropyl ether and hexane, and these fractions are discarded, and then with 3.5 liters of pure diisopropyl ether which are concentrated to dryness under reduced pressure (0.2 kPa). 59.3 g of a viscous residue are obtained. The latter is dissolved in 490 cm$^3$ of ethanol. 25.4 cm$^3$ of 10N sodium hydroxide are added and the solution is stirred for 3 hours at 20° C. The solvents are separated off and a solution of 22 cm$^3$ of hydrochloric acid (d=1.18) in 110 cm$^3$ of water is added to the residue. The precipitate is drained, washed with water and dried under vacuum over phosphorus pentoxide. 49.1 g of 7-[4,5-bis(4-methoxyphenyl)-2-oxazolyl]-2-cyanoheptanoic acid are obtained in the form of a whitish powder, melting point 150° C. with effervescence (decarboxylation).

1,2-Bis(4-methoxyphenyl)-2-(6-bromohexanamido)ethanone may be prepared in the following manner: a solution of 41.5 g of pyridine in 50 cm$^3$ of dichloromethane is added in the course of 50 minutes to a suspension, cooled to 5° C. and stirred, of 64.6 g of 2-amino-1,2-Bis(4-methoxyphenyl)ethanone hydrochloride (obtained according to G. DREFAHL and M. HARTMAN, Ann. Chem., 1954, 589, p. 82–90) in 250 cm$^3$ of dichloromethane containing 47 g of 6-bromohexanoyl chloride. The mixture is stirred for 20 hours at room temperature. 60 cm$^3$ of water are added, and the organic phase is separated after settling has taken place and washed with twice 50 cm$^3$ of normal hydrochloric acid and then with water (twice 30 cm$^3$). The organic phase is dried over magnesium sulphate and the solvent is evaporated off. The solid residue is recrystallised in a mixture of diisopropyl ether (1300 cm$^3$) and isopropanol (80 cm$^3$). 84.9 g (90%) of 1,2-bis(4-methoxyphenyl)-2-(6-bromohexanamido)ethanone, melting point 93° C., are obtained.

EXAMPLE 2

The procedure is as in Example 1. A mixture of 3.4 g of 6-[4,5-Bis(4-methoxyphenyl)-2-oxazolyl]hexanenitrile, 1.45 g of sodium azide and 1.76 g of ammonium chloride in 70 cm$^3$ of dimethylformamide is heated to 105° C. for 60 hours. After the addition of sodium azide and ammonium chloride (in the same quantities as before), the mixture is brought again to 105° C. for 60 hours. At room temperature, the mixture is diluted with 210 cm$^3$ of water, acidified with 2N hydrochloric acid and extracted with ethyl acetate (3 times 50 cm$^3$), and the reaction product is purified as described in Example 1. The solid isolated is recrystallised in 60 cm$^3$ of ethyl acetate, and 1.7 g (44.8%) of 5-{5-[4,5-bis(4-methoxyphenyl)-2-oxazolyl]pentyl}tetrazole, a white solid, melting point 150° C. are obtained.

6-[4,5-Bis(4-methoxyphenyl)-2-oxazolyl]hexanenitrile is prepared in the following manner:

A solution of 5 g of 4,5-Bis(4-methoxyphenyl)-2-(5-bromopentyl)oxazole in 23 cm$^3$ of ethanol and 1.1 g of potassium cyanide dissolved in 9 cm$^3$ of water are brought to reflux for 15 hours. After evaporation of the solvent, the organic/inorganic residue is dissolved in 40 cm$^3$ of diethyl ether and 10 cm$^3$ of water, and the ether phase is separated and washed with 10 cm$^3$ of saturated sodium chloride solution, dried over magnesium sulphate, filtered and concentrated to dryness. The viscous residue (4.4 g) is chromatographed on a column of useful diameter 2 cm containing 80 g of silica gel (50 to 200μ). The column is eluted with 1.2 liters of diazopropyl ether, collecting 50 cm$^3$ fractions. The fractions emerging at between 0.2 and 1.2 liters are concentrated to dryness. 3.5 g (80%) of 6-[4,5-bis(4-methoxyphenyl)-2-oxazolyl]hexanenitrile are obtained in the form of a pale yellow oil.

EXAMPLE 3

1.5 g of 7-[4,5-bis(4-chlorophenyl)-2-oxazolyl]hexanenitrile in 30 cm$^3$ of dimethylformamide are treated with twice 0.73 g sodium azide and twice 0.60 g of ammonium chloride according to the (heating and time) conditions defined in Example 2. The crude product isolated (1.6 g) is chromatographed on a column 2 cm in diameter containing 20 g of silica gel (50 to 200μ). The column is eluted, collecting 100 cm$^3$ fractions, first with 0.9 liter of diisopropyl ether and then with 0.6 liter of ethyl acetate. The ethyl acetate eluates are concentrated to 30 cm$^3$, the solution is cooled and 0.8 g (48%) of 5-{6-[4,5-bis(4-chlorophenyl)-2-oxazolyl]hexyl}tetrazole is obtained in the form of white crystals, melting point 148° C.

7-[4,5-Bis(4-chlorophenyl)-2-oxazolyl]-heptanenitrile may be prepared in the following manner: 8.8 g of 4,5-bis(4-chlorophenyl)-2-(5-bromopentyl)oxazole are dissolved in 60 cm$^3$ of dimethylformamide containing 14.1 g of tert-butyl cyanoacetate. 2.8 g of potassium carbonate and 0.8 g of tetrabutylammonium iodide are added to the solution. The mixture is stirred for 32 hours at 45°–50° C. After cooling, 200 cm$^3$ of water are added and the mixture is extracted with diethyl ether (3 times 50 cm$^3$). The organic extracts are washed with water (3 times 20 cm$^3$), dried over magnesium sulphate, filtered and concentrated to dryness. The residue is chromatographed on a column 3 cm in diameter containing 200 g of silica gel (50 to 200μ).

The column is eluted, collecting 100 cm$^3$ fractions, with 2 liters of a diethyl ether/hexane (20:80 by volume) mixture. The fractions emerging at between 0.5 and 2 liters are concentrated to dryness. 10 g of a yellowish oil are obtained.

The latter is dissolved in 20 cm$^3$ of pure formic acid and the solution is stirred at 20° C. for 21 hours. It is concentrated to dryness by heating to 170° C. until the evolution of carbon dioxide has ceased. The residue is cooled, 20 cm$^3$ of water are then added to it and the mixture is extracted with ethyl ether (3 times 20 cm$^3$). The combined organic extracts are washed with 50 cm$^3$ of saturated aqueous sodium bicarbonate solution and with 20 cm$^3$ of water, dried over magnesium sulphate, filtered and concentrated to dryness. The residue is chromatographed on a column (diameter 2 cm) containing 64 g of silica gel (50 to 200μ). The column is eluted with 0.9 liter of methylene chloride, collecting 50 cm$^3$ fractions. The fractions emerging at between 0.4 and 0.9 liter are concentrated to dryness. 1.6 g (20%) of 7-[4,5-bis(4-chlorophenyl)-2-oxazolyl]heptanenitrile are obtained in the form of a white powder, melting point 64° C.

4,5-Bis(4-chlorophenyl)-2-(5-bromopentyl)oxazole is prepared in the following manner: 39.5 g of 1,2-bis(4-chlorophenyl)-2-(6-bromohexanamido)ethanone in 80 cm$^3$ of toluene containing 40 g of phosphorus oxychloride are stirred for 3 hours at 80° C. After evaporation to dryness under vacuum, 100 cm$^3$ of ice-cold water are added. The mixture is extracted with diethyl ether (3 times 120 cm$^3$) and the ethereal solutions are washed successively with water (3 times 50 cm$^3$) and saturated aqueous sodium bicarbonate solution (twice 100 cm$^3$). The organic phase is dried and concentrated to dryness. The solid residue is dissolved in 400 cm$^3$ of hexane, the solution is treated with animal charcoal and filtered through kieselguhr, the filtrate is cooled to 10° C. and the precipitate is drained and dried. 33 g (87%) of 4,5-bis(4-chlorophenyl)-2-(5-bromopentyl)oxazole are obtained in the form of white crystals, melting point 98° C.

1,2-Bis(4-chlorophenyl)-2-(6-bromohexanamido)ethanone may be prepared in the manner described for the keto amide of Example 1. Starting with 37.1 g of 2-amino-1,2-bis(4-chlorophenyl)ethanone hydrochloride (prepared according to M. J. HATCH and D. J. CRAM, J. Amer. Chem. Soc., 1953, 75, p. 38 to 44), 26.2 g of 6-bromohexanoyl chloride and 140 cm$^3$ of methylene chloride, 23.4 g of pyridine in 30 cm$^3$ of methylene chloride are added. The procedure is as in Example 1, and the solid residue from the treatments is crystallised in 300 cm$^3$ of diisopropyl ether. 40.5 g (75%) of 1,2-bis(4-chlorophenyl)-2-(6-bromohexanamido)ethanone, white crystals, melting point 105° C., are obtained.

EXAMPLE 4

The procedure is as in Example 2, heating for 48 hours 2.4 g of 6-[4,5-bis(4-chlorophenyl)-2-oxazolyl]hexanenitrile, 1.2 g of sodium azide and 1 g of ammonium chloride in 45 cm$^3$ of dimethylformamide. Sodium azide and ammonium chloride are added (in the same quantities as before) and the mixture is brought again to 105° C. for 48 hours. The reaction product is extracted as in the abovementioned example and crystallised in 80 cm$^3$ of diisopropyl ether. 1.2 g of 5-{5-[4,5-bis(4-chlorophenyl)-2-oxazolyl]pentyl}tetrazole, white crystals, melting point 100° C., are obtained.

6-[4,5-Bis(4-chlorophenyl)-2-oxazolyl]hexanenitrile may be prepared according to Example 2, by heating to reflux for 12 hours 4.4 g of 4,5-bis(4-chlorophenyl)-2-(5-bromopentyl)oxazole of Example 3 in 40 cm$^3$ of ethanol with the addition of 0.9 g of potassium cyanide dissolved in 8 cm$^3$ of water. After recrystallisation in 50 cm$^3$ of diisopropyl ether, 2.5 g (64%) of 6-[4,5-bis(4-chlorophenyl)-2-oxazolyl]hexanenitrile, white crystals, melting point 108° C., are obtained.

EXAMPLE 5

The procedure is as in the preceding example, heating 1 g of 7-(4,5-diphenyl-2-oxazolyl)heptanenitrile, twice 0.9 g of sodium azide and twice 0.7 g of ammonium chloride in 20 cm$^3$ of dimethylformamide. The solid residue derived from the extractions is crystallised in a mixture of ethyl acetate (5 cm$^3$) and diisopropyl ether (15 cm$^3$). 0.4 g (35%) of 5-[6-(4,5-diphenyl-2-oxazolyl)- hexyl]tetrazole is obtained in the form of white crystals, melting point 132° C.

7-(4,5-Diphenyl-2-oxazolyl)heptanenitrile may be prepared according to Example 3:

From 15 g of 2-(6-bromohexanamido)-1,2-diphenylethanone and 17.8 g of phosphorus oxychloride in 35 cm$^3$ of toluene (4 hours at 80° C.), 11.5 g of a yellowish oil are obtained. 7.4 g of this oil are heated to 50° C. for 26 hours with stirring in 60 cm$^3$ of dimethylformamide containing 14.1 g of tert-butyl cyanoacetate, 0.8 g of tetrabutylammonium iodide and 2.8 g of potassium carbonate. The residue from the organic extracts of the reaction is chromatographed on a column 3 cm in diameter containing 200 g of silica gel. The column is eluted, collecting 100 cm$^3$ fractions, with 2.5 liters of a mixture of diisopropyl ether and hexane (vol/vol). The fractions emerging at between 1.5 and 2.5 liters are concentrated to dryness. 2.5 g of a yellowish oil are obtained.

This oil is dissolved in 50 cm$^3$ of xylene containing 0.1 g of p-toluenesulphonic acid and the mixture is heated to reflux for 7 hours. After evaporation to dryness, 60 cm$^3$ of saturated sodium bicarbonate solution and 120 cm$^3$ of diethyl ether are added. The ethereal solution is washed with 30 cm$^3$ of water, dried over magnesium sulphate and concentrated to dryness. The residue is chromatographed on a column 2 cm in diameter containing 50 g of silica gel (50 to 200µ). The column is eluted, collecting 50 cm$^3$ fractions, with 0.4 liter of diisopropyl ether and then 0.5 liter of ethyl acetate. The ethyl acetate eluates are concentrated to dryness and 1 g of a thick, yellowish oil is obtained, this oil being employed directly in the initial step of the example.

2-(6-Bromohexanamide)-1,2-diphenylethanone may be prepared according to Example 1:

From 12.9 g of aminodeoxybenzoin hydrochloride (prepared according to H. O. HOUSE and W. F. BERKOWITZ, J. Org. Chem., 28, 307 (1963)) and 11.7 g of 6-bromohexanoyl chloride in 65 cm$^3$ of methylene chloride and 10.3 g of pyridine in 15 cm$^3$ of methylene chloride, and after crystallisation in 100 cm$^3$ of diisopropyl ether, 15.1 g (74.6%) of 2-(6-bromohexanamido)-1,2-diphenylethanone are obtained in the form of white crystals, melting point 92° C.

EXAMPLE 6

4 g of 7-[4-(4-chlorophenyl)-5-(4-methoxyphenyl)-2-oxazolyl]heptanenitrile, twice 2 g of sodium azide and twice 1.7 g of ammonium chloride in 50 cm$^3$ of dimethylformamide are heated according to Example 5. The solid residue derived from the organic extracts 3 times 75 cm$^3$ of diethyl ether is crystallised in 50 cm$^3$ of toluene and 2.5 g (56%) of 5-{6-[4-(4-chlorophenyl)-5-(4-methoxyphenyl)-2-oxazolyl]hexyl}tetrazole, white crystals, melting point 132° C., are obtained.

7-[4-(4-Chlorophenyl)-5-(4-methoxyphenyl)-2-oxazolyl]heptanenitrile may be prepared in three steps according to the reaction sequence of Example 2.

4 g of pyridine in 5 cm$^3$ of dichloromethane are added to a suspension, stirred and cooled to 5° C., of 6.2 g of 2-amino-2-(4-chlorophenyl)-1-(4-methoxyphenyl)ethanone hydrochloride (G. DREFAHL, G. HEUBLEIN, K. FRITZSCHE and R. SIEMANN, J. Prakt. Chem. 1966, 32, p. 307 to 310) in 50 cm$^3$ of dichloromethane containing 4.9 g of 7-bromoheptanoyl chloride. The product is isolated according to the abovementioned example. 8 g of a thick, yellowish-brown oil are obtained. A solution of the latter in 50 cm$^3$ of toluene is treated with 5 cm$^3$ of phosphorus oxychloride. The product derived from the reaction is purified by chromatography on a column 2.8 cm in diameter containing silica gel 150 g of (50 to 200µ). The column is eluted, collecting 50 cm$^3$ fractions, with 0.5 liter of a mixture containing equal parts (vol/vol) of diisopropyl ether and hexane. The fractions emerging at between 0.2 and 0.5 liter are concentrated to dryness and 7 g of a pale yellow oil are obtained. The latter is dissolved in 50 cm$^3$ of ethanol, a solution of 1.5 g of potassium cyanide in 10 cm$^3$ of water is added and the mixture is brought to reflux for 6 hours. The product of the reaction is chromatographed on a column 2.8 cm in diameter containing 120 g of silica gel (50 to 200µ). The column is eluted, collecting 100 cm$^3$ fractions, first with 1.6 liters of a mixture containing equal parts of diisopropyl ether and hexane, and then with 0.5 liter of diethyl ether. The fractions originating from the latter solvent are concentrated to dryness and 4.3 g (55%) of 7-[4-(4-chlorophenyl)-5-(4-methoxyphenyl)-2-oxazolyl]heptanenitrile are obtained in the form of a solid, melting point 35° C.

EXAMPLE 7

4 g of 6-[4-(4-chlorophenyl)-5-(4-methoxyphenyl)-2-oxazolyl]hexanenitrile, twice 2 g of sodium azide and twice 1.7 g of ammonium chloride in 50 cm$^3$ of dimethylformamide are heated according to Example 5. The product of the reaction is purified by chromatography on a column 2 cm in diameter containing 40 g of silica gel (50 to 200µ). The column is eluted, collecting 25 cm$^3$ fractions, first with 0.2 liter of diisopropyl ether and then with 0.3 liter of ethyl acetate. The ethyl acetate eluates are concentrated to dryness and the solid residue is crystallised in 40 cm$^3$ of ethanol. 2 g (45%) of 5-{5-[4-(4-chlorophenyl)-5-(4-methoxyphenyl)-2-oxazolyl]pentyl}tetrazole, white crystals, melting point 160° C., are obtained.

6-[4-(4-Chlorophenyl)-5-(4-methoxyphenyl)-2-oxazolyl]hexanenitrile may be prepared in the following manner:

8 g of 2-(6-bromohexanamido)-2-(4-chlorophenyl)-1-(4-methoxyphenyl)ethanone and 5 cm$^3$ of phosphorus oxychloride in 100 cm$^3$ of toluene are heated to 80° C. for 6 hours. The mixture is concentrated to dryness under reduced pressure and 50 cm$^3$ of ice-cold water and 150 cm$^3$ of diethyl ether are added. The ethereal extract is washed with 100 cm$^3$ of saturated aqueous sodium bicarbonate solution. After drying over magnesium sulphate and concentration to dryness under vacuum, 7 g of a pale yellow oil are obtained. The latter is dissolved in 50 cm$^3$ of ethanol, and 1.5 g of potassium cyanide in 5 cm$^3$ of water are added. The mixture is heated to reflux for 6 hours, then concentrated to dryness and 50 cm$^3$ of water and 100 cm$^3$ of diethyl ether are added. The organic phase is dried over magnesium sulphate and concentrated to dryness. The residue is crystallised in 30 cm$^3$ of hexane. 5 g of white crystals, melting point 50° C., are obtained.

2-(6-Bromohexanamido)-2-(4-chlorophenyl)-1-(4-methoxyphenyl)ethanone may be prepared according to Example 6:

From 6.2 g of 2-amino-2-(4-chlorophenyl)-1-(4-methoxyphenyl)ethanone hydrochloride [prepared according G. DREFAhL et al., J Prakt. Chem. 32, 307 (1966)] in 50 cm$^3$ of methylene chloride containing 4.5 g of 6-bromohexanoyl chloride and 4 g of pyridine in 5 cm$^3$ of methylene chloride, 8.5 g (93%) of 2-(6-bromohexanamido)-2-(4-chlorophenyl)-1-(4-methoxyphenyl)ethanone, white crystals, melting point 96° C., are obtained.

EXAMPLE 8

15 g of 6-[5-(4-chlorophenyl)-4-(4-methoxyphenyl)-2-oxazolyl]hexanenitrile, twice 7.5 g of sodium azide and twice 6.2 g of ammonium chloride in 150 cm$^3$ of dimethylformamide are heated according to Example 7. The product of the reaction is purified by chromatography on a column 2 cm in diameter containing 150 g of silica gel. The column is eluted, collecting 50 cm$^3$ fractions, with 0.8 liter of ethyl acetate. The fractions emerging at between 0.2 and 0.8 liter are concentrated to dryness, the residue is crystallised in 70 cm$^3$ of isopropyl acetate and 4.5 g (27%) of 5-{6-[5-(4-chlorophenyl)-4-(methoxyphenyl)-2-oxazolyl]hexyl}tetrazole, white crystals, melting point 122° C., are obtained.

7-[5-(4-Chlorophenyl)-4-(4-methoxyphenyl)-2-oxazolyl]heptanenitrile may be prepared according to Example 6:

Starting with 35 g of 2-amino-1-(4-chlorophenyl)-2-(4-methoxyphenyl)ethanone hydrochloride in 150 cm$^3$ of dichloromethane containing 27.2 g of 7-bromoheptanoyl chloride, 22.5 g of pyridine in 30 cm$^3$ of dichloromethane are added. The product of the reaction is purified by chromatography on a column 2.8 cm in diameter containing 300 g of silica gel. The column is eluted, collecting 50 cm$^3$ fractions, with 1.2 liters of diisopropyl ether. The fractions emerging at between 0.2 and 1.2 liters are concentrated to dryness and 28.5 g of a yellowish oil are obtained. The latter is dissolved in 115 cm$^3$ of toluene and treated with 33 g of phosphorus oxychloride. The product of the reaction is chromatographed on a column 2.8 cm in diameter containing 150 g of silica gel. The column is eluted, collecting 50 cm$^3$ fractions, with 0.8 liter of diisopropyl ether. The fractions emerging between 0.3 and 0.8 liter are concentrated to dryness under reduced pressure. 18 g of a yellowish oil are obtained.

100 cm$^3$ of ethanol and a solution of 8 g of potassium cyanide in 20 cm$^3$ of water are added to this oil. The mixture is heated to reflux for 22 hours. The product of the reaction is chromatographed on a column 2 cm in diameter containing 150 g of silica gel.

The column is eluted, collecting 50 cm$^3$ fractions, with 0.9 liter of diisopropyl ether. The fractions emerging at between 0.25 and 0.9 liter are concentrated to dryness under reduced pressure and 15 g of a pale yellow oil are obtained, the oil being used directly above for the synthesis of 5-{6-[5-(4-chlorophenyl)-4-(4-methoxyphenyl)-2-oxazolyl]hexyl}tetrazole.

2-Amino-1-(4-chlorophenyl)-2-(4-methoxyphenyl)ethanone hydrochloride may be prepared in the following manner:

45 g of 2-acetylamino-1-(4-chlorophenyl)-2-(4-methoxyphenyl)ethanone, dissolved in 300 cm$^3$ of ethanol containing 135 cm$^3$ of hydrochloric acid (d=1.18), are heated to reflux for 7 hours. After filtration through kieselguhr and concentration to dryness under vacuum, 200 cm$^3$ of acetone are added to the solid residue, which is drained and washed with the same solvent, twice 75 cm$^3$. 36 g (80%) of 2-amino-1-(4-chlorophenyl)-2-(4-methoxyphenyl)ethanone hydrochloride, an amorphous white powder, melting point 230° C., are obtained.

2-Acetylamino-1-(4-chlorophenyl)-2-(4-methoxyphenyl)ethanone may be prepared from 1-(4-chlorophenyl)-2-(4-methoxyphenyl)ethanone (G. G. SMITH, F. D. BAGLEY and R. TAYLOR, J. Amer. Chem. Soc., 1961, 83, p. 3647), in the following manner: according to the process for nitrosation of a ketone with an alkyl nitrite in the presence of an alcoholate (C. F. KOELSCH and C. D. LE CLAIRE, J. Org. Chem., 6, 531 (1941)), the solution of 40 g of 1-(4-chlorophenyl)-2-(4-methoxyphenyl)-ethanone in 160 cm$^3$ of ethanol is added at 20° C. to a solution of 40 g of sodium ethylate (prepared from 7.8 g of sodium and 240 cm$^3$ of ethanol). After stirring of the mixture for 1 hour, 38.8 g of butyl nitrite is added so as to maintain the exothermic reaction at between 30 and 40° C., and stirring is then continued for 16 hours at room temperature. The mixture is poured into 1.2 liters of water containing 21 cm$^3$ of acetic acid. The resulting mixture is extracted with methylene chloride (3 times 150 cm$^3$), the combined organic extracts are washed with 120 cm$^3$ of saturated sodium bicarbonate solution and then with twice 60 cm$^3$ of water and dried over magnesium sulphate and the solvent is evaporated off under vacuum. 44 g of a yellowish, pasty residue are obtained, this residue being used directly in the following reaction: according to a method described for converting benzil monooxime to acetamidodeoxybenzoin (H. O. HOUSE and W. F. BERKOWITZ, J. Org. Chem., 1963, 28, p. 307), the product (44 g) of the above reaction is dissolved in 200 cm$^3$ of acetic acid containing 216 g of acetic anhydride. 40 g of finely powdered zinc (44µ) are added to the stirred solution in the course of 2 hours so as to maintain the exothermic reaction at between 40° and 50° C. After 4 hours stirring at 20° C., the mixture is filtered through sintered glass. The filtrate is concentrated to one half, 400 cm$^3$ of ethanol are added and the mixture is brought to reflux for 1 hour. It is concentrated to dryness under reduced pressure, the residue is dissolved in 800 cm$^3$ of methylene chloride and the organic solution is washed with saturated sodium bicarbonate solution (3 times 150 cm$^3$) and with 100 cm$^3$ of water, dried over magnesium sulphate and concentrated to dryness under reduced pressure. The solid residue is crystallised in 290 cm$^3$ of ethanol. 46 g (94%) of 2-acetylamino-1-(4-chlorophenyl)-2-(4-methoxyphenyl)ethanone are obtained in the form of white crystals, melting point 140° C.

EXAMPLE 9

10 g of (RS)-7-[4,5-bis(4-methoxyphenyl)-2-oxazolyl]-2-methylheptanenitrile (10 g) in 50 cm$^3$ of dimethylformamide are treated with twice 4.8 g of sodium azide and twice 10.2 g of triethylamine hydrochloride according to the (time and temperature) conditions defined in Example 1. After treatment, the product of the reaction is chromatographed on a column 2.8 cm in diameter containing 90 g of silica gel (50 to 200µ). The column is eluted with 1.8 liters of diisopropyl ether and then with 2.2 liters of a diisopropyl ether/ethyl acetate (30:70 by volume) mixture, collecting 200 cm$^3$ fractions. The fractions from the last eluent mixture are concentrated to dryness under reduced pressure (0.2 kPa). The residue obtained (8.4 g) is dissolved in 178 cm$^3$ of 0.1N sodium hydroxide and the solution is concentrated to dryness under reduced pressure (0.2 kPa). The product obtained is suspended in 50 cm$^3$ of diisopropyl ether with stirring, drained, washed with twice 20 cm$^3$ of diisopropyl ether and dried. 8.1 g (69%) of (RS)-5-{7-[4,5-bis(4-methoxyphenyl)-2-oxazolyl]-2-heptyl}-1H-tetrazole sodium salt is obtained in the form of white crystals, melting point 104° C.

(RS)-7-[4,5-Bis(4-methoxyphenyl)-2-oxazolyl]-2-methylheptanenitrile may be prepared as follows:

15 g of phosphorus oxychloride is added with stirring to a solution of 13.8 g of (RS)-1,2-bis(4-methoxyphenyl)-2-(7-cyanooctanamido)ethanone in 65 cm$^3$ of toluene, and the mixture is heated to 80° C. for 4 hours. The solution is poured onto 50 g of ice, the toluene phase is separated after settling has taken place and the aqueous phase is extracted with twice 50 cm$^3$ of ethyl acetate. The combined organic extracts are washed with water (3 times 20 cm$^3$) and with 30 cm$^3$ of saturated aqueous sodium chloride solution. After drying over sodium sulphate, the solvent is evaporated off under reduced pressure. The residue is chromatographed on a column 2.8 cm in diameter containing 100 g of silica gel (50 to 200). The column is eluted, collecting 50 cm$^3$ fractions, with 1.8 liters of diisopropyl ether. The fractions emerging at between 0.3 liter and 1.8 liters are concentrated under reduced pressure (0.2 kPa). 12.4 g (93%) of (RS)-7-[4,5-bis(4-methoxyphenyl)-2-oxazolyl]-2-methylheptanenitrile are obtained in the form of a yellowish oil, which is used directly in the subsequent reaction.

Proton NMR spectrum (300 MHz, CDCl$_3$, δ in ppm, J in Hz):

1.3 (d, J=6.5, 3H, —CH$_3$)
1.35 to 1.75 (mt, 6H, central =CH$_2$ groups)
1.87 (mt, 2H, =CH$_2$ β to the oxazole)
2.6 (mt, 1H, —CH<)
2.83 (t, J=7, 2H, =CH$_2$ α to the oxazole)
3.84 (s, 6H, —OCH$_3$)
6.91 (d, J=8.5, 4H, aromatic ortho to the —OCH$_3$ groups)
7.51 and 7.56 (2d, J=8.5, 4H, aromatic)

(RS)-1,2-Bis(4-methoxyphenyl)-2-(7-cyanooctanamido)ethanone may be prepared as follows:

14.4 g of 7-cyanooctanoic acid dicyclohexylamine salt are added to a mixture of 45 cm$^3$ of a molar solution of sodium hydrogen sulphate and 100 cm$^3$ of diethyl ether. The mixture is stirred for 15 minutes at 20° C. and the organic phase is then separated. The latter is dried over magnesium sulphate and filtered and the solvent is evaporated off under reduced pressure. The residue, treated with 24.6 g of thionyl chloride is heated to 50° C. for 3 hours. The mixture is evaporated under reduced pressure. The residual oil is dissolved in 10 cm$^3$ of dichloromethane, and the solution obtained is added to a suspension, stirred and cooled to 5° C., of 12.1 g of 2-amino-1,2-bis(4-methoxyphenyl)ethanone hydrochloride in 50 cm$^3$ of dichloromethane containing 7.8 g of pyridine. The mixture is stirred for 20 hours at room temperature, 40 cm$^3$ of water are then added and the organic phase is separated after settling has taken place and washed with 20 cm$^3$ of normal hydrochloric acid and with water (3 times 20 cm$^3$). The organic phase is dried over magnesium sulphate and filtered and the solvent is evaporated off under reduced pressure. The residue is chromatographed on a column 2.8 cm in diameter containing 100 g of silica gel (50 to 200μ). The column is eluted, collecting 200 cm$^3$ fractions, with 4 liters of a diisopropyl ether/ethyl acetate (80:20 by volume) mixture. The fractions emerging at between 0.6 liter and 4 liters are concentrated under reduced pressure (0.2 kPa). 13.9 g (83%) of (RS)-1,2-bis(4-methoxyphenyl)-2-(7-cyanooctanamido)ethanone are obtained in the form of a yellowish oil, which is used directly in the subsequent reaction.

Proton NMR spectrum (200 MHz, CDCl$_3$, δ in ppm, J in Hz):

1.28 (d, J=7, 3 H, —CH$_3$)
1.25 to 1.75 (mt, 8H, =CH$_2$)
2.24 (t, J=7.5, 2H, =NCO—CH$_2$—)
2.55 (mt, 1H, —CH<)
3.74 and 3.81 (2s, 3H each, —OCH$_3$)
6.46 (d, J=7, 1H, —CO—CH—N—CO—)
6.82 and 6.87 (2d, J=9, 4H, aromatic ortho to the —OCH$_3$ groups)
6.99 (broad d, J=7, —CONH—)
7.3 (d, J=9, 2H, aromatic)
7.95 (d, J=9, 2H, aromatic ortho to the C=O)

7-Cyanooctanoic acid dicyclohexylamine salt may be prepared as follows:

100 g of ethyl 6-bromohexanoate and 253.4 g of ethyl cyanoacetate are dissolved in 900 cm$^3$ of dimethylformamide, and 61.9 g of potassium carbonate and 16.5 g of tetrabutylammonium iodide are added to the mixture. The suspension is stirred at 60° C. for 5 hours. After cooling, 2.7 liters of water are added and the mixture is extracted with diethyl ether (3 times 200 cm$^3$). The combined ethereal extracts are washed with 3 times 100 cm$^3$ of water and then with 100 cm$^3$ of saturated aqueous sodium chloride solution. After drying over magnesium sulphate, the solvent is evaporated off under reduced pressure. The evaporation residue is distilled under reduced pressure (0.01 kPa) at 144° C. 95.1 g (83%) of a colourless oil are obtained. The latter is dissolved in 740 cm$^3$ of dimethylformamide, and 51.1 g of potassium carbonate, 13.7 g of tetrabutylammonium iodide and 105 g of methyl iodide are added to the mixture. The suspension is stirred at 20° C. for 18 hours, 2.2 liters of water are added and the mixture is extracted with diethyl ether (3 times 200 cm$^3$). The combined ethereal extracts are washed with 6 times 100 cm$^3$ of water and then with 100 cm$^3$ of saturated aqueous sodium chloride solution. After drying over magnesium sulphate, the solvent is evaporated off to dryness. The evaporation residue is distilled under reduced pressure (0.01 kPa) at 130° C. 93.3 g (93%) of a colourless oil are obtained. The latter is dissolved in 430 cm$^3$ of ethanol and a solution of 56.5 g of 86% pure potassium hydroxide in 40 cm$^3$ of water is added. The mixture is stirred for 48 hours at 20° C., acidified with 74 cm$^3$ of 12N hydrochloric acid and concentrated to dryness under reduced pressure. 40 cm$^3$ of water are added to the residue, the mixture is extracted with diethyl ether (3 times 100 cm$^3$) and the combined ethereal extracts are washed with 3 times 30 cm$^3$ of water, dried over magnesium sulphate, filtered and concentrated to dryness. The evaporation residue is heated to 160° C. for 3 hours until the evolution of carbon dioxide has ceased, and the product is then distilled under reduced pressure (0.01 kPa) at between 205 and 210° C. 46.8 g of the acid are obtained, which are dissolved in 250 cm$^3$ of diethyl ether with 37.6 g of dicyclohexylamine. The mixture is left stirring for 1 hour and the precipitate is drained. The filtrate is treated again with 50 g of dicyclohexylamine and left standing overnight. The dicyclohexylamine salt which precipitates is drained, washed with twice 50 cm$^3$ of diethyl ether and dried. 51.4 g (42%) of 7-cyanooctanoic acid dicyclohexylamine salt are obtained in the form of a white powder, melting point 85° C.

EXAMPLE 10

4.45 g of (RS)-7-[4,5-bis(4-chlorophenyl)-2-oxazolyl]-2-methylheptanenitrile in 40 cm$^3$ of dimethylformamide are treated with twice 2.1 g of sodium azide and twice 4.4 g of triethylamine hydrochloride under the (time and temperature) conditions defined in Example 1. After treatment, the product of the reaction is chromatographed on a column 2.8 cm in diameter containing 115 g of silica gel (50 to 200μ). The column is eluted with 1.2 liters of diisopropyl ether and then with 2.8 liters of a diisopropyl ether/ethyl acetate (80:20 by volume) mixture, collecting 200 cm³ fractions. The fractions from the last eluent mixture are concentrated to dryness under reduced pressure (0.2 kPa). 2.7 g (55%) of (RS)-5-{7-[4,5-bis(4-chlorophenyl)-2-oxazolyl]-2-heptyl}-1H-tetrazole are obtained in the form of white crystals, melting point 144° C.

(RS)-7-[4,5-Bis(4-chlorophenyl)-2-oxazolyl]-2-methylheptanenitrile may be prepared according to the conditions defined in Example 9:

8 g of phosphorus oxychloride are added with stirring to a solution of 7.5 g (RS)-1,2-bis(4-chlorophenyl)-2-(7-cyanooctanamido)ethanone in 35 cm³ of toluene, and the mixture is heated to 90° C. for 6 hours. After treatment, the product obtained is chromatographed on a column 2.8 cm in diameter containing 110 g of silica gel (50 to 200μ). The column is eluted with 0.6 liter of diisopropyl ether, collecting 50 cm³ fractions. The fractions emerging at between 0.15 liter and 0.6 liter are concentrated under reduced pressure (0.2 kPa). 6.6 g (91%) of (RS)-7-[4,5-bis(4-chlorophenyl)-2-oxazolyl]-2-methylheptanenitrile are obtained in the form of a yellowish oil, which is used directly in the subsequent reaction.

Proton NMR spectrum (300 MHz, CDCl$_3$, δ in ppm, J in Hz):

1.32 (d, J=7, 3 H, —CH$_3$)
1.4 to 1.8 (mt, 6H, central =CH$_2$ groups)
1.87 (mt, 2H, =CH$_2$ β to the oxazole)
2.61 (mt, 1H, —CH<)
2.85 (t, J=7, 2H, =CH$_2$ α to the oxazole)
7.34 (d, J=8.5, 4H, aromatic ortho to the Cl atoms)
7.49 and 7.54 (2d, J=8.5, 4H, aromatic)

(RS)-1,2-Bis(4-chlorophenyl)-2-(7-cyanooctanamido)ethanone may be prepared according to the conditions defined in Example 9:

8.2 g of 7-cyanooctanoic acid dicyclohexylamine salt are added to a mixture of 26 cm³ of a molar solution of sodium hydrogen sulphate and 60 cm³ of diethyl ether. The mixture is stirred for 15 minutes at 20° C. and the organic phase is then separated. The latter is dried over magnesium sulphate and filtered and the solvent is evaporated off under reduced pressure. The residue is treated with 13.2 g of thionyl chloride and heated to 50° C. for 3 hours. The mixture is concentrated under reduced pressure. The residual oil is dissolved in 5 cm³ of dichloromethane, and the solution obtained is added to a suspension, stirred and cooled at 5° C. of 7 g of 2-amino-1,2-bis(4-chlorophenyl)ethanone hydrochloride in 25 cm³ of dichloromethane containing 4.4 g of pyridine. After treatment, the product obtained is chromatographed on a column 2.8 cm in diameter containing 140 g of silica gel (50 to 200μ). The column is eluted with 1 liter of diisopropyl ether and then with 2.5 liters of a diisopropyl ether/ethyl acetate (90:10 by volume) mixture, collecting 250 cm³ fractions. The fractions from the last eluent mixture are concentrated to dryness under reduced pressure (0.2 kPa). 7.6 g (80%) of (RS)-1,2-bis(4-chlorophenyl)-2-(7-cyanooctanamido)ethanone are obtained in the form of a yellowish oil, which is used directly in the subsequent reaction.

Proton NMR spectrum (300 MHz, CDCl$_3$, δ in ppm, J in Hz):

1.26 (d, J=7, 3H, —CH$_3$)
1.2 to 1.7 (mt, 8H, central =CH$_2$ groups)
2.22 (t, J=7.5, 2H, =NCO—CH$_2$—)
2.51 (mt, 1H, —CH<)
6.44 (d, J=7, 1H, —CO—CH—N—CO—)
6.90 (broad d, J=7, 1H, —CONH—)
7.25 (d, J=8.5, 4H, aromatic ortho to the Cl atoms)
7.35 (d, J=8.5, 2H, aromatic)
7.85 (d, J=8.5, 2H, aromatic ortho to the C=O).

EXAMPLE 11

3 g of (RS)-7(4,5-diphenyl-2-oxazolyl)-2-methylheptanenitrile in 30 cm³ of dimethylformamide are treated with twice 1.7 g of sodium azide and twice 3.6 g of triethylamine hydrochloride under the (time and temperature) conditions defined in Example 1. After treatment, the product of the reaction is chromatographed on a column 2 cm in diameter containing 78 g of silica gel (50 to 200μ). The column is eluted, collecting 200 cm³ fractions, with 1 liter of diisopropyl ether and then with 1.6 liters of a diisopropyl ether/ethyl acetate (95:5 by volume) mixture. The fractions from the last eluent mixture are concentrated to dryness under reduced pressure (0.2 kPa). 2.3 g (68%) of (RS)-5-[7-(4,5-diphenyl-2-oxazolyl)-2-heptyl]-1H-tetrazole are obtained in the form of a yellowish oil.

Proton NMR spectrum (200 MHz, CDCl$_3$, δ in ppm, J in Hz):

1.37 (d, J=7, 3H, —CH$_3$)
1.1 to 1.95 (mt, 8H, central =CH$_2$ groups)
2.85 (t, J=7.5, 2H, =CH$_2$ α to the oxazole)
3.17 (mt, 1H, —CH<)
7.35 (mt, 6H, aromatic)
7.57 (mt, 4H, aromatic ortho to the substitutions)

(RS)-7-(4,5-Diphenyl-2-oxazolyl)-2-methylheptanenitrile may be prepared under the conditions defined in Example 9:

7.3 g of phosphorus oxychloride are added to a solution of 5.75 g of (RS)-1,2-diphenyl-2-(7-cyanooctanamido)ethanone in 30 cm³ of toluene, and the mixture is heated to 80° C. for 6 hours. After treatment, the product obtained is chromatographed on a column 2 cm in diameter containing 60 g of silica gel (50 to 200μ). The column is eluted with 0.6 liter of diisopropyl ether, collecting 50 cm³ fractions. The fractions emerging at between 0.1 liter and 0.6 liter are concentrated under reduced pressure (0.2 kPa). 4.2 g (76%) of (RS)-7-(4,5-diphenyl-2-oxazolyl)-2-methylheptanenitrile are obtained in the form of an oil, which is used directly in the subsequent reaction.

Proton NMR spectrum (200 MHz, CDCl$_3$, δ in ppm, J in Hz):

1.34 (d, J=6.5, 3H, —CH$_3$)
1.4 to 2 (mt, 8H, central =CH$_2$ groups)
2.64 (mt, 1H, —CH<)
2.9 (t, J=7.5, 2H, =CH$_2$ α to the oxazole) 7.4 (mt, 6H, aromatic)
7.6 and 7.65 (2d, J=8.5, 4H, aromatic)

(RS)-1,2-Diphenyl-2-(7-cyanooctanamido)ethanone may be prepared under the conditions defined in Example 9:

9 g of 7-cyanooctanoic acid dicyclohexylamine salt is added to a mixture of 28 cm³ of a molar solution of sodium hydrogen sulphate and 60 cm³ of diethyl ether. The mixture is stirred for 15 minutes at 20° C. and the organic phase is then separated. The latter is dried over magnesium sulphate and filtered and the solvent is evaporated off under reduced pressure. The residue is treated with 14.8 g of thionyl chloride and heated to 50° C. for 3 hours. The mixture is concentrated under reduced pressure. The residual oil is dissolved in 6 cm³ of dichloromethane, and the solution obtained is added to a suspension, stirred and cooled to 5° C. of 6 g of 2-amino-1,2-diphenylethanone hydrochloride in 30 cm³ of dichloromethane containing 4.8 g of pyridine. After treatment, the product obtained is chromatographed on a column 2 cm in diameter containing 48 g of silica gel (50 to 200μ). The column is eluted, collecting 100 cm³ fractions, with 1.2 liters of a diisopropyl ether/ethyl acetate (80:20 by volume) mixture. The fractions emerging at between 0.3 and 1.2 liters are concentrated under reduced pressure (0.2 kPa). 5.9 g (67%) of (RS) -1,2-diphenyl-2-(7-cyanooctanamido)ethanone are obtained in the form of an oil, which is used directly in the subsequent reaction.

Proton NMR spectrum (200 MHz, CDCl₃, δ in ppm and J in Hz):

1.2 (d, J=7, 3H, —CH₃)
1.1 to 1.7 (mt, 8H, central =CH₂ groups)
2.18 (t, J=7.5, 2H, =NCO—CH₂—)
2.48 (mt, 1H, —CH<)
6.5 (d, J=7, 1H, —CO—CH—N—CO—)
6.95 (broad d, J=7, 1H, —CONH—)
7.05 to 7.55 (mt, 8H, aromatic)
7.9 (d, J=8.5, aromatic ortho to the C=O group)

EXAMPLE 12

5 g of 7-[4,5-bis(4-methoxyphenyl)-2-oxazolyl]-2,2-dimethylheptanenitrile in 12 cm³ of dimethylformamide are treated with twice 2.7 g of sodium azide and twice 4.95 g of triethylamine hydrochloride according to the (time and temperature) conditions defined in Example 1. After treatment, the product of the reaction is chromatographed on a column 3.5 cm in diameter containing 120 g of silica gel (50 to 200μ). The column is eluted, collecting 50 cm³ fractions, with 0.5 liter of diisopropyl ether and then with 1.3 liters of a diisopropyl ether/ethyl acetate (70:30 by volume) mixture. The fractions emerging at between 0.85 liter and 1.3 liters are concentrated under reduced pressure (0.2 kPa). The solid is taken up with 30 cm³ of diethyl ether and drained, washed with 10 cm³ of diethyl ether and dried. 2.8 g (50%) of 5-{7-[4,5-bis(4-methoxyphenyl)-2-oxazolyl]-2-methyl-2heptyl}-1H-tetrazole are obtained in the form of white crystals, melting point 82° C.

7-[4,5-Bis(4-methoxyphenyl)-2-oxazolyl]-2,2-dimethylheptanenitrile may be prepared as follows:

A mixture of 2.9 g of isobutyronitrile in 35 cm³ of tetrahydrofuran and 21 cm³ of a 2 molar solution of lithium diisopropylamide in hexane is maintained for 1 hour at −40° C. The solution is cooled to −70° C. and then treated in the course of 20 minutes with a solution of 15 g of 4,5-bis(4-methoxyphenyl)-2-(5-bromopentyl)oxazole (prepared as in Example 1) in 30 cm³ of tetrahydrofuran. The solution is brought back to room temperature in the course of 2 hours and taken up with 150 cm³ of water and then with 200 cm³ of diethyl ether. The organic phase is separated after settling has taken place, dried over magnesium sulphate, filtered and concentrated to dryness under reduced pressure. The residue is chromatographed on a column 2.8 cm in diameter containing 100 g of silica gel (50 to 200μ). The column is eluted, collecting 50 cm³ fractions, with 0.7 liter of diisopropyl ether. The fractions emerging at between 0.35 liter and 0.7 liter are concentrated under reduced pressure (0.2 kPa). 6 g (42%) of 7-{4,5-bis(4-methoxyphenyl)-2-oxazolyl]-2,2-dimethylheptanenitrile are obtained in the form of a yellowish oil, which is used directly in the subsequent reaction.

Proton NMR spectrum (300 MHz, CDCl₃, δ in ppm and J in Hz):

1.35 (s, 6H, =C(CH₃)₂)
1.4 to 1.65 (mt, 6H, central =CH₂ groups)
1.87 (mt, 2H, =CH₂ β to the oxazole)
2.85 (t, J=7.5, 2H, =CH₂ α to the oxazole)
3.85 (s, 6H, —OCH₃)
6.90 (d, J=9, 4H, aromatic ortho to the —OCH₃ groups)
7.5 and 7.55 (2d, J=9, 4H, aromatic)

The present invention also relates to pharmaceutical compositions consisting of a product of the general formula (I), or a salt, optionally in combination with any other compatible product which can be inert or physiologically active. The compositions according to the invention may be used parenterally, orally, rectally or topically.

As solid compositions for oral administration, tablets, pills, powders or granules may be used. In these compositions, the active product according to the invention is mixed with one or more inert diluents or adjuvants such as sucrose, lactose or starch. These compositions can also comprise substances other than diluents, for example a lubricant such as magnesium stearate.

As liquid compositions for oral administration, emulsions of a pharmaceutically acceptable nature, solutions, suspensions, syrups and elixirs, containing inert diluents such as water or liquid paraffin, may be used. These compositions can also comprise substances other than diluents, for example wetting, sweetening or flavouring products.

The compositions for parenteral administration can be sterile solutions, aqueous or nonaqueous, suspensions or emulsions. As a solvent or vehicle, propylene glycol, a polyethylene glycol, vegetable oils, especially olive oil, and injectable organic esters, for example ethyl oleate, may be employed. These compositions can also contain adjuvants, especially wetting, emulsifying or dispersing agents. The sterilisation may be carried out in several ways, for example using a bacteriological filter, by incorporating sterilising agents in the composition, by irradiation or by heating. They may also be prepared in the form of sterile solid compositions which will be dissolved at the time of use in sterile water or any other sterile injectable medium.

The compositions for rectal administration are suppositories or rectal capsules, which can contain, apart from the active product, excipients such as cocoa butter or Suppocire.

The compositions for topical administration can be, for example creams, ointments or lotions.

In human therapy, the products according to the invention may be especially useful in the treatment of diseases of inflammatory origin. They may hence prove very useful in osteoarticular pathology in the treatment of arthritis, rheumatoid arthritis, spondylarthritis, gout, osteoarthritis and chondrocalcinosis, as well as in other inflammatory pathologies affecting the lungs, the digestive tract (ulcerative colitis, liver inflammation, cirrhosis, diseases of the colon, Crohn's disease), the skin (psoriasis, herpes, acne, erythema, eczema, dermatitis), the eyes, the nasal passages, the buccal cavity and the teeth. They may also be used in treatments for nasal and bronchial allergies (asthma). The products according to the invention may also be useful in treatments for inflammations linked to the introduction of implants, by improving their compatibility with the surrounding tissue. They may also play a part in immunoregulation (autoimmune diseases), ischaemia and reperfusion (cardiac in particular).

These products also exert a beneficial effect in the treatment of hyperthermia and pain.

The doses depend on the effect sought and the treatment period. For an adult, they are generally between 500 mg and 1 g per day administered orally. Generally speaking, the physician will determine the dose he considers most suitable in accordance with the age and weight and all other factors specific to the subject to be treated.

The example which follows illustrates a composition according to the invention.

EXAMPLE

Tablets of active product having the following composition are prepared according to the usual technique:

| | |
|---|---|
| 5-{6-[4,5-Bis(4-methoxyphenyl)-2-oxazolyl]-hexyl}tetrazole | 100 mg |
| Starch | 332 mg |
| Silica | 120 mg |
| Magnesium stearate | 12 mg |

We claim:

1. A Compound of the formula:

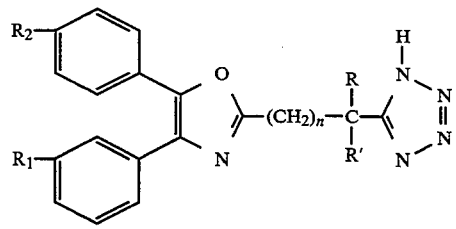

where:
R and R' are identical or different and are hydrogen or alkyl having 1 or 2 carbon atoms;
$R_1$ and $R_2$ are identical or different and are hydrogen, halogen or alkyloxy having 1 to 4 carbon atoms in a straight or branched chain;
n equals 3 to 6; and its isomers and racemic mixtures; or a pharmaceutically acceptable salt thereof.

2. A compound according to claim 1, where:
R and R' are hydrogen or methyl;
$R_1$ and $R_2$ are hydrogen, halogen or methoxy; and
n equals 4 or 5.

3. A compound according to claim 1 which is 5-{6-[4,5-bis(4-methoxyphenyl)-2-oxazolyl]hexyl}tetrazole.

4. A compound according to claim 1 which is 5-{7-[4,5-bis(4-methoxyphenyl)-2-oxazolyl]-2-heptyl}-1H-tetrazole.

5. A Compound according to claim 1 which is 5-{7-[4,5-bis(4-methoxyphenyl)-2-oxazolyl]-2-methyl-2-heptyl}-1H-tetrazole.

6. A Compound according to claim 1 which is 5-{5-[4,5-bis(4-methoxyphenyl)-2-oxazolyl]pentyl}tetrazole.

7. A compound according to claim 1 which is 5-{6-[4-(4-chlorophenyl)-5-(4-methoxyphenyl)-2-oxazolyl]hexyl}tetrazole.

8. A pharmaceutical composition for the treatment of diseases of inflammatory origin wherein the active ingredient is an effective amount of at least one compound of claim 1 in admixture with a pharmaceutical carrier.

* * * * *